United States Patent [19]

McCarthy et al.

[11] Patent Number: 5,332,857
[45] Date of Patent: Jul. 26, 1994

[54] 3,5-DIHYDROXY-6,8-NONADIENOIC ACIDS AND DERIVATIVES AS HYPOCHOLESTEROLEMIC AGENTS

[75] Inventors: Peter A. McCarthy, Pawcatuck; Frederick J. Walker, Preston, both of Conn.

[73] Assignee: Pfizer Inc., New York, N.Y.

[21] Appl. No.: 909,254

[22] Filed: Jul. 6, 1992

Related U.S. Application Data

[62] Division of Ser. No. 499,489, Mar. 27, 1990, Pat. No. 5,151,545.

[51] Int. Cl.$^5$ .............................................. C07C 69/76
[52] U.S. Cl. .................................. 560/60; 562/465; 562/467; 562/469; 562/470; 562/472; 562/586; 562/587; 560/56; 560/183; 549/12; 549/26; 549/354; 549/388; 554/219
[58] Field of Search .................... 560/56, 60, 183; 549/12, 26, 354, 388; 514/532, 431, 437, 450, 454, 569; 554/219

[56] References Cited

U.S. PATENT DOCUMENTS

| 4,198,425 | 4/1980 | Mitsui et al. | 424/279 |
|---|---|---|---|
| 4,255,444 | 3/1981 | Oka et al. | 424/279 |
| 4,294,846 | 10/1981 | Albers-Schonberg et al. | 424/279 |
| 4,351,844 | 9/1982 | Patchett et al. | 424/279 |
| 4,375,475 | 3/1983 | Willard et al. | 424/279 |
| 4,459,422 | 7/1984 | Willard et al. | 560/59 |
| 4,654,363 | 3/1987 | Prugh | 514/460 |
| 5,151,545 | 9/1992 | McCarthy et al. | 560/60 |

OTHER PUBLICATIONS

Stokker, J. Med. Chem. vol. 28, pp. 347–358 (1985).

*Primary Examiner*—Paul J. Killos
*Attorney, Agent, or Firm*—Peter C. Richardson; Gregg C. Benson; D. Stuart McFarlin

[57] ABSTRACT

Variously substituted 3,5-dihydroxy-6,8-nonadienoic acids and esters, are blood cholesterol lowering agents and so are useful in the prevention and treatment of cardiovascular diseases such as atherosclerosis.

11 Claims, No Drawings

3,5-DIHYDROXY-6,8-NONADIENOIC ACIDS AND DERIVATIVES AS HYPOCHOLESTEROLEMIC AGENTS

This is a division, of application Ser. No. 07/499,489 filed on Mar. 27, 1990, U.S. Pat. No. 5,151,545.

BACKGROUND OF THE INVENTION

Variously substituted 3,5-dihydroxy-6,8-nonadienoic acids and derivatives, as defined by the formula (I) below, possess hypocholesterolemic (blood cholesterol lowering) activity and so are useful in the prevention and treatment of certain cardiovascular diseases such as atherosclerosis.

Previously reported as hypocholesterolemic compounds have been variously substituted 6-phenyl-, 6-(2-phenethyl)-, 6-(3-phenylpropyl)- and 6-(2-styryl)-4-hydroxy-6-hexanolides including, in particular,

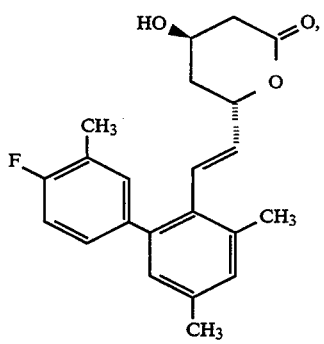

and the corresponding ring opened 3,5-dihydroxy-omega-substituted- (hexan-, heptan-, octan- and 6-hepten-)oic acids [Willard et al., U.S. Pat. Nos. 4,375,475 and 4,459,422; see also Mitsui et al., U.S. Pat. No. 4,198,425; Stokker et al., J. Med. Chem., vol. 28, pp. 347–358 (1985)].

SUMMARY OF THE INVENTION

The present invention is directed to hypocholesterolemic compounds having the relative stereochemical formula

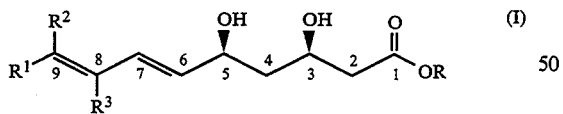

wherein R is hydrogen, $(C_1-C_3)$alkyl, phenyl, benzyl or a conventional radical forming an ester group which is hydrolyzable under physiological conditions;

$R^1$ and $R^2$, when taken separately, and $R_3$ are each independently hydrogen, $(C_1-C_3)$alkyl, benzyl, naphthyl, phenyl or phenyl mono or disubstituted with the same or different substituents selected from the group consisting of F, Cl, Br, I, $(C_1-C_3)$alkyl, $CF_3$, $(C_1-C_3)$alkoxy, benzyl and phenyl; with the proviso that at least one of $R^1$ and $R^2$ is other than hydrogen or $(C_1-C_3)$alkyl; and $R^1$ and $R^2$ when taken together, are combined with the double bonded carbon atom which they are attached to form a diradical ylidene group of the formula

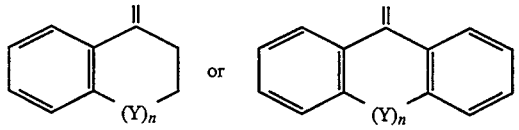

wherein n is 0 or 1 and Y is oxygen, $OCH_2$, sulfur, $SCH_2$, methylene $(CH_2)$ or ethylene $(CH_2CH_2)$; and the pharmaceutically acceptable cationic salts thereof when R is hydrogen.

Exemplary of such ylidene groups are

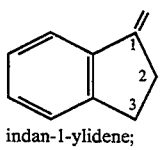

indan-1-ylidene;

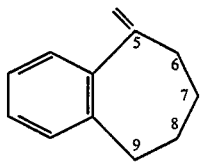

8,9-dihydro-6H-benzocyclohepten-5(7H)-ylidene;

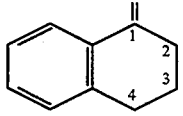

3,4-dihydronaph-1(2H)-ylidene;

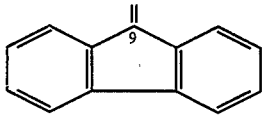

9-fluorenylidene;

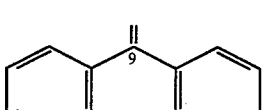

9(10H)-anthracenylidene;

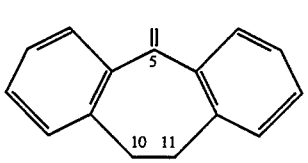

10H-dibenzo[a,d]cyclohepten-5(11H)ylidene

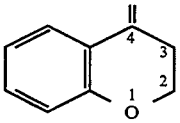

4-chromanylidene;

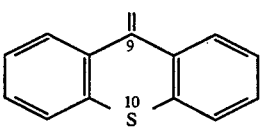

9-thioxanthenylidene;

-continued and

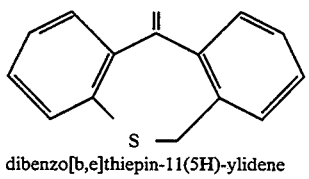

dibenzo[b,e]thiepin-11(5H)-ylidene all named according to the "IUPAC Nomenclature of Organic Chemistry", 1979 Edition, Pergammon Press, New York, N.Y., 1979, pp. 17, 21, 23, 27, 30, 57 and 62. It is understood that formula (I) represents relative stereochemistry and that the compounds of the present invention are racemic, comprised of equal portions of enantiomers (i.e., compounds which are mirror images, equally rotating plane polarized light, but in opposite directions). It is to be expected that the pharmacological activity resides primarily in one of these two enantiomers. It is also to be understood that the geometry about the C6-C7 double bond is that shown in the formula (I); i.e., the trans or E geometric isomer.

Preferred compounds, because of their ease of preparation and level of hypocholesterolemic activity, have R as methyl or hydrogen and $R^3$ as hydrogen. Within those classes, preferred compounds have $R^1$ and $R^2$ as each phenyl, 4-chlorophenyl or 4-fluorophenyl, or taken together with the double bonded carbon to which they are attached to form a 9-xanthenylidene group or an 8,9-dihydro-6H-benzocyclohepten-5(7H)-ylidene group.

Pharmaceutically-acceptable cationic salts include, but are not limited to, those of sodium, potassium, calcium, N,N'-dibenzylethylenediamine, N-methylglucamine (meglumine) and diethanolamine. The preferred cationic salts are those of potassium and sodium.

The reference to esters which are hydrolyzable under physiological conditions refers to those esters frequently referred to as "pro-drugs". Such esters are now as well-known and common in the medicinal art as pharmaceutically-acceptable salts. Such esters are generally used to enhance oral absorption, but in any event are readily hydrolyzed in vivo to the parent acid. The more preferred ester forming radicals are those wherein R is:

furan-5(1H)-on-1-yl;
isobenzofuran-3(1H)-on-1-yl;
3,4-dihydro fur an-5 (1H) -on-1-yl;
—$CHR^4$ $OCOR^5$; or
—$CHR^4OCOOR^5$;

wherein $R^4$ is hydrogen or methyl; and $R^5$ is $(C_1-C_6)$alkyl. The most preferred radicals are pivaloyloxymethyl and 1-(ethoxycarbonyloxy) ethyl.

The present invention also encompasses pharmaceutical compositions for the treatment or prevention of atherosclerosis in a mammal which comprises a blood cholesterol lowering effective amount of a compound of the formula (I); and method of treating or preventing atherosclerosis in a mammal which comprises administering a blood cholesterol lowering effective amount of a compound of the formula (I) to said mammal.

The present invention is also directed to intermediates of the formula (IV), as specified below.

DETAILED DESCRIPTION OF THE INVENTION

The present invention is readily carried out. Thus, the compounds of formula (I) are prepared by initial reaction of an aldehyde of the formula

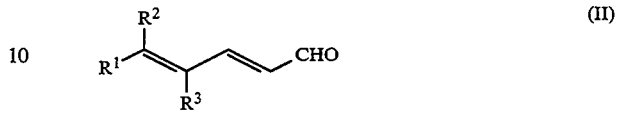

wherein $R^1$, $R^2$ $R^3$, and are as defined above, with an acetoacetate ester of the formula $$CH_3COCH_2COOR'$$ (III)

wherein R' is $(C_1-C_3)$ alkyl, phenyl or benzyl, thereby forming a compound of the formula

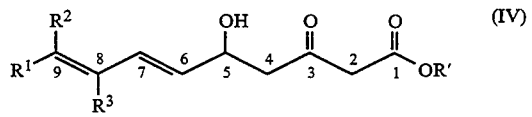

having 6E (C6–C7 trans) geometry as depicted. Where more than one geometry is also possible about the C8–C9 double bond, such will already have been specified in the ingoing aidehyde.

This condensation reaction is generally carried out under anhydrous conditions in a reaction-inert solvent, preferably a relatively polar ether such as tetrahydrofuran or 1,2-dimethoxyethane. Initially the acetoacetate ester (III) is reacted with at least one molar equivalent of a strong base such as sodium hydride to form the mono anion, and then with at least one molar equivalent of an equally strong or stronger, preferably soluble base, such as butyllithium in hexanes, to further form the dianion in situ. The latter is then reacted with aldehyde (II), forming the desired compound (IV). The reaction temperature is not critical, but is preferably below room temperature, e.g., $-25°$ to $+15°$ C. (conveniently at the temperature of a water-ice bath) in order to minimize possible side reactions. The product is isolated by conventional methods, e.g., by quenching into water, extraction into a water immiscible organic solvent and evaporation.

The intermediate beta-keto ester (IV) is then selectively reduced to form an ester of the formula (I) wherein R corresponds to R', as defined above. The reducing agent employed is one which will selectively reduce the 3-oxo group to the alcohol having the desired relative (3R*,5S*) relative stereochemistry. A particularly suitable method is to preform a complex of the compound (IV) with at least one molar equivalent of triethylborane (e.g., about 1.5 molar equivalents), in the presence of trimethylacetic acid (e.g., 0.1 to 0.15 molar equivalents), in situ, in a reaction inert solvent such as tetrahydrofuran. The temperature of complex formation is not critical, e.g., $0°-40°$ C., conveniently ambient temperature, is generally satisfactory. The complex is then reduced with sodium borohydride at greatly reduced temperature, e.g., at $-50°$ to $-100°$ C. Once reaction is complete, the desired product is isolated by conventional methods, e.g., by quenching with excess aqueous $H_2O_2$, followed by acidification with a strong aqueous acid, extraction into a water immiscible organic solvent and evaporation.

When a compound of the formula (I) wherein R is hydrogen (or a salt thereof) is desired, a corresponding compound of the formula (I) wherein R is $(C_1-C_3)$alkyl, benzyl or phenyl is hydrolyzed under conventional conditions, e.g., with substantially one molar equivalent of a strong base, such as aqueous sodium hydroxide, in a reaction inert solvent, e.g., aqueous ethanol. In some cases, the initially formed salt will precipitate directly from the reaction mixture and can be recovered by filtration, if desired. Alternatively, the salt is isolated by another conventional method, e.g., evaporation to dryness, or distillative displacement of a water miscible lower boiling organic solvent with water or steam distillation of a water-immiscible organic solvent, and freeze drying. If the free acid is desired, the hydrolysis reaction mixture is acidified and the acid conventionally isolated, e.g., by dilution with water, extraction into a water immiscible organic solvent and evaporation.

Salts of the compounds of the formula (I) are also readily prepared from the isolated acid forms by standard methods. For example, an equivalent of the corresponding cationic hydroxide, carbonate or bicarbonate, or of an amine, is combined with the carboxylic acid in an organic or aqueous solvent. The salt is isolated by concentration and/or the addition of a non-solvent.

The $(C_1-C_3)$alkyl, phenyl and benzyl esters encompassed by the formula (I) are also readily prepared from the acid forms by conventional methods. In those methods which involve reaction of an activated form of acid with a $(C_1-C_3)$alkanol, phenyl or benzyl alcohol, it is preferred to prepare the desired ester from an acid in which the 3-hydroxy group is in protected form (e.g., as the t-butyldimethyl silyl ether derivative), so as to avoid potential dimerization/polymerization as a side reaction. Such a protecting group is removed by mild acid hydrolysis, or treatment with fluoride ion, during isolation of the ester, or as a final step, care being taken to avoid acid conditions sufficiently vigorous to hydrolyze the desired ester group.

Mixed anhydrides are well-suited as the activated acid form in the preparation of said alkyl, phenyl and benzyl esters. Generally, the acids are first converted in situ to a tertiary amine salt in the presence of a 1 to 1.1 molar excess of the amine. A variety of tertiary amines are suitable for this purpose. Exemplary are triethylamine, N-methylpiperidine, N-methylmorpholine, dimethylaniline or quinoline. Suitable inert solvents are methylene chloride, chloroform, dimethylformamide, and dimethylacetamide. It is preferrable that the acid be completely dissolved by the excess of tertiary amine, which may require a stirring period, together with gentle warming, if necessary. The solution of amine salt is then reacted with an equivalent of alkyl (e.g. ethyl), benzyl, or phenyl chloroformate, at a temperature in the range of $-40°$ to $25°$ C., preferably in the range $-10°$ to $10°$ C., to form a mixed anhydride in solution. Without isolation, the mixed anhydride is reacted directly with the appropriate alcohol or phenol to yield the desired ester. The reaction is usually initiated at a cool temperature (such as $-40°$ to $15°$ C.), but allowed to warm to higher temperature (such as $15°$ to $40°$ C.) to complete the reaction.

The above alkyl and benzyl esters are alternatively prepared, and the esters wherein R is a conventional radical forming an ester which is hydrolyzable under physiological conditions are generally prepared, by reaction of a salt of the acid (I, R=H; preferably the tetrabutylammonium salt) with an appropriate compound containing a displaceable halide (iodide, bromide or chloride; generally preferred, where available, in that order), or another group suitable for nuclophilic displacement. Exemplary are $CH_3OSO_2CH_3$, $C_2H_5Br$, $CH_3CH_2CH_2I$, $ICHR^1OCOR^2$, $ICHR^1OCOOR^2$,

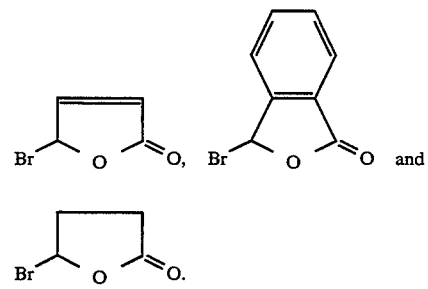

The required acid salt can be preformed, or more conveniently, formed in situ by use of at least one equivalent of a base. The reaction is carried out in a reaction-inert solvent, preferably one which is essentially anhydrous. A particularly convenient reaction system employs excess potassium carbonate as base in acetone as solvent. When the halide is chloro or bromo, up to three or more equivalents of anhydrous sodium iodide is added, if desired, to enhance the rate of reaction. An excess of the halide reagent is not critical to the reaction, but such an excess will generally be used in order to force the reaction to completion in a shorter period of time. The rate of reaction will also depend greatly on the halide (e.g., $I > Br > Cl$) and on the nature of the radical group R (e.g., more branched $ICHCH_3OCOCH_3$ will react more slowly than $ICH_2OCOCH_3$). The reaction temperature is not critical, a temperature in the range of $0°-100°$ C. being generally satisfactory.

The acetoacetate esters (III) required for synthesis of the present compounds are commercially available, or readily prepared by known methods. The aldehydes of the formula (II), where not previously known, are readily prepared by known methods, as exemplified in preparations below, e.g., according to the following scheme:

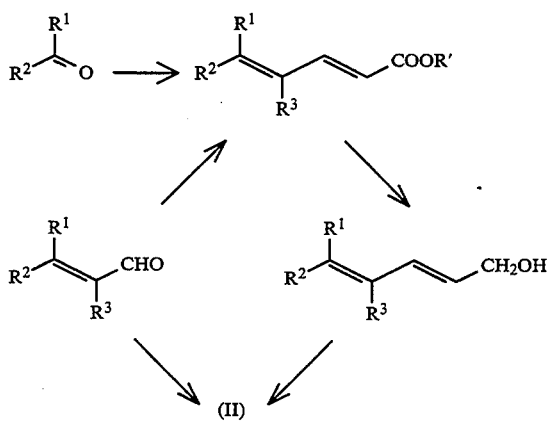

wherein $R^1$ $R^2$ $R^3$ and $R'$ are as defined above

The biological procedures for evaluating these compounds were as follows: Rat liver microsomal, HMG- CoA (3-hydroxy-3-methylglutaryl-coenzyme A) reductase was isolated, solubilized and purified through the heat fractionation methods of Rogers et al., Analytical Biochemistry, vol. 101, pp. 107–111 (1980). HMG-CoA reductase activity was measured according to the procedure of Harwood et al., J. Lipid. Res., vol. 25, pp. 967–978 (1984). Inhibition of rat cholesterol biosynthesis was measured using $^{14}C$-acetate according to the procedure of Endo et al., Eur. J. Blochem., vol. 77, pp. 31–36 (1977).

For use in the treatment or prevention of atherosclerosis in a mammal, including man, a compound of the formula (I) is administered in a blood cholesterol lowering (or a low blood cholesterol maintaining) amount of about 1–50 mg/kg/day, in single or divided daily doses. In particular cases, dosages outside that range are prescribed at the discretion of the attending physician. The preferred route of administration is generally oral, but parenteral administration (e.g. intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof. As used below, THF=tetrahydrofuran.

EXAMPLE 1

Methyl (E)-5-Hydroxy-9,9-diphenyl-3-oxo-6,8-nonadienoate

A 60% dispersion of sodium hydride (0.095 g of dispersion, 0.057 g of NaH, 2.4 mmol) was triturated with anhydrous THF (3×20 ml). The pure sodium hydride was then suspended in anhydrous THF (10 ml) and cooled to 0° C. Methyl acetoacetate (0.227 g, 1.95 mmol) was added dropwise. After stirring the resulting colorless solution for 10 minutes at 0° C., butyllithium in hexanes (0.96 ml, 2.5M, 2.4 mmol) was added dropwise via syringe. After stirring the reaction mixture for another 10 minutes at 0° C., a solution of 5,5-diphenyl-2,4-pentadienal (0.410 g, 1.75 mmol) in anhydrous tetrahydrofuran (10 ml) was added slowly via syringe. After completion of the addition, the reaction was stirred for 10 minutes at 0° C. The reaction mixture was then quenched by pouring it into saturated aqueous ammonium chloride. After stirring vigorously for 5 minutes, the phases were separated and the aqueous phase was extracted with ether (3×25 ml). The combined organic phases were washed with saturated aqueous sodium bicarbonate (40 ml) and water (2×40 ml), dried over magnesium sulfate and concentrated in vacuo to give 0.610 g (98% yield) of methyl (E)-5-hydroxy-9,9-diphenyl-3-oxo-6,8-nonadienoate as a viscous liquid. Since this material was quite pure and unstable on silica gel, it was carried onto the next step without purification.

Another lot was purified by PTLC (1:2 ethyl acetate:hexane, 10% recovery) and gave the following spectral data: High resolution mass spectra: m/e 350.1554, calcd. for $C_{22}H_{22}O_4$ 350.1518. $^1H$-NMR ($CDCl_3$), delta: 7.40–7.15 (m, 10H), 6.65 (d, 12Hz, 1H)); 6.50 (dd, 16 & 12Hz, 1H); 5.90 (dd, 16 & 6.6Hz, 1H);4.65 (ddd, 6.6, 6.0 & 1Hz); 3.70 (s, 3H); 3.45 (s, 2H); 2.77 (dd, 15 & 6.0Hz, 1H); 2.73 (dd, 15 & 1Hz, 1H). $^{13}C$-NMR ($CDCl_3$), delta: 202.4, 167.3, 143.1, 139.5, 135.0, 130.4, 129.6, 129.1, 128.3, 127.6, 126.8, 68.5, 52.5, 49.8, 49.6. IR ($CHCl_3$) $cm^{-1}$: 3019, 2949, 1748, 1714, 1629, 1491, 1363.

EXAMPLE 2

Methyl (3R*,5S*)-(E)-3,5-Dihydroxy-9,9-diphenyl-6,8-nonadienoate

To a room temperature solution of the title product of the preceding Example (3.00 g, 8.56 mmol) in anhydrous THF (100 ml) was added triethylborane (12.7 ml of 1.0M solution in tetrahydrofuran, 12.7 mmol) and trimethylacetic acid (0.13 g, 1.27 mmol) under nitrogen. The pale yellow solution was stirred under nitrogen for 2 hours. The resulting complex was cooled to −90° C. and sodium borohydride (0.374 g, 10.0 mmol) and methanol (37 ml) were added. After stirring for 45 minutes at −90° C., the reaction mixture was warmed to −60° C. and quenched by careful addition of aqueous hydrogen peroxide (21 ml of 30% $H_2O_2$ mixed with 53 ml of water). After stirring for 45 minutes at room temperature, this mixture was partitioned between 1M HCl (200 ml) and ethyl acetate (500 ml). The phases were separated and the organic phase was washed with saturated aqueous sodium bicarbonate (100 ml) and water (2×100 ml), dried over magnesium sulfate and concentrated in vacuo to give 2,996 g (99.2% yield of present title product, m.p. 87°–89° C.

The product of this reaction did not require purification, but lots derived from earlier experiments were purified by PTLC (1:1 ether:hexane). High resolution mass spectra: m/e 352.1662, calcd. for $C_{22}H_{24}O_4$ 352.1674. $^1H$-NMR ($CDCl_3$), delta 7.4–7.1 (m, 10H); 6.64 (d, 12Hz, 1H); 6.30 (dd, 15 & 12Hz, 1H); 5.85 (dd, 15 & 6.6Hz, 1H); 4.35 (ddd, 1H); 4.22 (ddd, 1H); 3.82 (s, 1H); 3.65 (s, 3H); 3.32 (s, 1H); 2.45 (dd, 2H); 1.65 (m, 2H). $^{13}C$-NMR ($CDCl_3$), delta: 172.8, 143.4, 142.1, 137.7, 130.3, 128.5, 128.2, 128.1, 127.9, 127.8, 127.6, 127.5, 127.0, 72.6, 68.3, 51.8, 42.5, 41.5. IR ($CHCl_3$) $cm^{-1}$: 3330, 3040, 1745, 1595, 1495.

EXAMPLE 3

(3R* 5S*)-(E)-3 5-Dihydroxy-9 9-diphenyl-6,8-nonadienoic Acid

To a solution of the title product of the preceding Example (0.244 g, 0.69 mmol) in ethanol (5 ml) was added 1M sodium hydroxide (0.7 ml, 0.70 mmol). As the reaction mixture was stirred for 30 minutes, it developed into a suspension of the sodium salt of present title product (which, with or without concentration, is optionally isolated by filtration). This suspension was cautiously acidified with 1M hydrochloric until the pH was approximately 4 as judged by pH paper. The mixture was then diluted with water (10 ml) and extracted with ether (3×25 ml). The combined extracts were washed with water (2×25 ml), dried with magnesium chloride and concentrated to give 0.226 g (97% yield) of present title product.

A portion of this lot (0.160 g) was purified by PTLC (2:1 ether:hexane) to give 140 mg (88% recovery) of product which gave the following data: High resolution mass spectra: m/e found 338.1489, calc. for $C_{21}H_{22}O_4$ 338.1518. $^1$H-NMR (DMSO-d$_6$), delta: 7.50–7.10 (m, 10H); 6.81 (d, 12Hz, 1H); 6.19 (dd, 12 & 15Hz, 1H); 5.99 (dd, 15 & 6Hz, 1H); 4.84 (br s, 1H); 4.15 (m, 1H); 3.90 (m, 1H); 2.36 (dd, 6 & 17Hz, 1H); 2.22 (dd, 9 & 17Hz, 2H); 1.64–1.40 (m, 2H). $^{13}$C-NMR (CDCl$_3$), delta 172.9, 141.7, 140.8, 140.3, 139.2, 130.0, 128.4, 128.3, 127.6, 127.4, 127.3, 127.0, 126.2, 68.4, 65.2, 44.5, 42.7. IR (CHCl$_3$) cm$^{-1}$: 3450–3150, 2920, 1730, 1600, 1495.

EXAMPLE 4

Methyl (E)-5-Hydroxy-9,9-di(4-chlorophenyl)-3-oxo-6,8-nonadienoate

Using a procedure identical to the one described in Example 1, 5,5-di (4-chlorophenyl)-2,4-pentadienal (1.071 g, 3.5 mmole) was converted into 1.523 g (100% yield) of title product. This material was taken on to the next step without purification.

Purification of another lot by PTLC (1:1 ether:hexane) yielded product which gave the following data: High resolution mass spectra: m/e found 418.0744, calcd. for $C_{22}H_{20}Cl_2O_4$ 418.0739. $^1$H-NMR (CDCl$_3$), delta: 7.46–7.07 (m, 8H); 6.64 (d, 10Hz, 1H); 6.33 (dd, 15 & 10Hz, 1H); 5.92 (dd, 15 & 6Hz, 1H); 4.65 (dt, 6 & 5Hz, 1H); 3.75 (s, 3H); 3.50 (s, 2H); 2.79 (d, 5Hz, 1H); 1.75 (br s, 1H). $^{13}$C-NMR (CDCl$_3$), delta: 141.2, 140.2, 137.5, 136.2, 133.7, 131.7, 128.8, 128.7, 128.5, 128.3, 127.7, 68.2, 52.5, 49.7, 49.3. IR (neat on NaCl plates) cm$^{-1}$: 3500, 3020, 2950, 1745, 1710 1485.

EXAMPLE 5

Methyl (3R*,5S*)-(E)-3,5-Dihydroxy-9,9-di (4-chlorophenyl)-6,8-nonadienoate

Using a procedure identical to the one described in Example 2, title product of the preceding Example (1.15 g, 2.74 mmol) was converted into 1.15 g of crude product. Purification by flash chromatography (2:1 ether:hexane) gave 0.626 g (54% yield) of purified present title product.

$^1$H-NMR-(CDCl$_3$), delta: 7.42–704 (m, 8H); 6.65 (d, 11Hz, 1H); 6.30 (dd, 15 & 11Hz, 1H); 5.91 (dd, 15 & 7Hz, 1H); 4.43 (m, 1H); 4.29 (m, 1H); 3.72 (s, 3H); 3.31 (br s, 1H); 2.52 (d, 7Hz, 2H); 1.80–1.58 (m, 3H). $^{13}$C-NMR (CDCl$_3$), delta: 173.4, 138.1, 131.7, 128.7, 128.6, 128.4, 127.9, 127.6, 72.3, 68.3, 51.9, 42.5, 41.4. IR (CHCl$_3$) cm$^{-1}$: 3480, 2950, 2880, 1720, 1595, 1485.

EXAMPLE 6

Methyl (E)-5-Hydroxy-9,9-di(4-fluorophenyl)-3-oxo-6,8-nonadienoate

Using a procedure identical to the one described in Example 1, 5,5-di(4-fluorophenyl)-2,4-pentadienal (0.576 g, 4.0 mmol) was converted into 1.47 g (100% yield) of title product. This material was taken on to the next step without purification.

Purification of another lot by PTLC (1:1 ether:hexane) yielded product which gave the following data: High resolution mass spectra: m/e found 386.1399, calcd. for $C_{22}H_{20}F_2O_4$ 386.1330. $^1$H-NMR (CDCl$_3$), delta: 7.19–6.81 (m, 8H); 6.49 (d, 12Hz, 1H); 6.22 (dd, 15 & 12Hz, 1H); 5.77 (dd, 15 & 6Hz, 1H); 4.55 (dt, 6 & 6Hz, 1H); 4.67 (s, 3H); 4.43 (s, 2H); 2.76 (br s, 1H); 2.71 (d, 6Hz, 2H). $^{13}$C-NMR (CDCl$_3$), delta: 174.5, 171.4, 167.3, 164.1, 163.9, 160.8, 160.6, 141.5, 138.1, 138.0, 135.4, 135.2, 135.1, 132.0, 131.9, 129.2, 129.1, 128.5, 126.9, 115.5, 115.3, 115.2, 115.0, 91.2, 68.2, 52.4, 49.6, 49.4 (fluorine not decoupled). IR (CHCl$_3$) cm$^{-1}$: 3440, 3020, 2950, 2930, 2870, 1730, 1695, 1585, 1490, 1425.

EXAMPLE 7

Methyl (3R* 5S*)-(E)-3 5-Dihydroxy-9,9-di (4-fluorophenyl)-6,8-nonadienoate

Using a procedure identical to the one described in Example 2, title product of the preceding Example (1.33 g, 3.4 mmol) was converted into 1.43 g of crude product. Purification by flash chromatography (5:1 ether:hexane) gave 0.74 g (56% yield) of present title product; m.p. 71°–72° C.

High resolution mass spectra: m/e found 388.1495, calcd. for $C_{22}H_{22}F_2O_4$ 388.1486. $^1$H-NMR (CDCl$_3$), delta: 7.25–6.86 (m, 8H); 6.56 (d, 11Hz, 1H); 6.28 (dd, 14 & 1Hz, 1H); 5.85 (dd, 14 & 6Hz, 1H); 4.44–4.33 (m, 1H); 4.30–4.17 (m, 1H); 3.69 (s, 3H); 3.22 (br s, 1H); 2.49 (d, 6Hz, 2H); 1.77–1.49 (m, 3H). $^{13}$C-NMR (CDCl$_3$), delta: 172.8, 164.0, 163.9, 160.1, 141.1, 138.2, 138.1, 137.2, 135.2, 135.1, 132.0, 131.9, 129.1, 129.0, 127.9, 127.2, 115.5, 115.3, 115.2, 115.0, 72.4, 68.3, 51.8, 42.55, 41.4 (fluorine not decoupled). IR(CHCl$_3$) cm$^{-1}$: 3370, 3030, 2940, 2910, 2850, 1890, 1710, 1585, 1495.

EXAMPLE 8

Methyl (E,E)-8-(8,9-Dihydro-6H, 7H-benzocyclo-hepten-5-ylidene)-5-hydroxy-3-oxo-6-octenoate By the method of Example 1 (E,E)-4-(8,9-Dihydro-6H,7H-benzocyclohepten-5-ylidene)-2-butenal (0.9 g, 4.2 mmol) was reacted with methyl acetoacetate to produce title product, 0.9 g.

$^1$H-NMR (CDCl$_3$) delta: 7.09–7.02 (m, 4H); 6.75 (dd, 17, 12Hz 1H); 6.02 (d, 10Hz, 1H); 5.73 (dd, 17, 7Hz, 1H); 4.73 (m, 1H); 3.76 (s, 3H); 3.52 (s, 2H); 2.85 (d, 7Hz, 1H); 2.80–2.48 (m, 5H); 1.80–1.76 (m, 4H). M.S. calcd. for $C_{20}H_{24}O_4$: 328.4072; Found 328.1730. Anal Calcd. for $C_{20}H_{24}O_4$: C, 73.15; H, 7.37. Found: C, 73.09; H, 7.19.

EXAMPLE 9

Methyl (3R*,5S*)-(E,E)-8-(8,9-Dihydro-6H,7H-benzocyclohepten-5-ylidene)-3,5-dihydroxy-6-octenoate By the method of Example 2, title product of the preceding Example (0.1 g, 0.3 mmol) was converted to present title product, 30 mg.

$^1$H-NMR (CDCl$_3$) delta: 7.20–7.00 (m, 4H); 6.61 (dd, 17, 13Hz, 1H); 6.03 (d, 13Hz, 1H); 5.72 (dd, 17, 7Hz, 1H); 4.54 (m, 1H); 4.31 (m, 1H); 3.71 (s, 3H); 2.51–2.74 (m, 9H); 1.71–1.82 (m, 5H). M.S. calcd. for $C_{20}H_{26}O_4$: 330.4230; Found 330.1859).

EXAMPLE 10

Sodium (3R*,5S*)-(E,E)-8-(8,9-Dihydro-6H,7H-benzocyclohepten-5-ylidene)-5-hydroxy-3-oxo-6-octenoate The product of the preceding Example (0.90 g, 2.7 mmol) in 20 ml of methanol was treated with aqueous NaOH (1N, 2.7 ml, 2.7 mmol) in one portion. After stirring for 0.5 hour, title product was recovered as an oil by evaporation in vacuo, 0.88 g.

$^1$H-NMR (DMSO-d$_6$) 7.16–7.01 (m, 4H); 6.49 (dd, 8, Hz, 1H); 6.00 (d, 6Hz, 1H); 6.75 (dd, 8, 3Hz, 1H); 5.00 (bs, 1H); 4.29–4.00 (m, 1H); 3.81–3.70 (m, 1H); 3.40 (bs, 1H); 2.72–2.39 (m, 4H); 2.95–1.38 (m, 8H). Anal. calcd.

for $C_{19}H_{23}O_4Na \cdot H_2O$: C, 63.56; H, 6.54. Found: C, 64.03; H, 6.15.

EXAMPLE 11

Methyl (E)-8-(10H,11H-Dibenzo[a,c]cyclohepten-5-ylidene)-5-hydroxy-3-oxo-6-octenoate By the method of Example 1, (E)-(10H,11H-dibenzo[a,c]cyclohepten-5-ylidene)-2-butenal (1.25 g, 4.8 mmol) was reacted methyl acetoacetate. Chromatography on silica gel (1:4, ethyl a cetate:hexane as eluant) provided title product (0.6 g).

$^1$H-NMR (CDCl$_3$) delta 7.9–7.0 (m, 8H); 6.5–6.29 (m, 2H); 5.79 (dd, 14, 7Hz, 1H); 4.63–4.55 (m, 1H); 3.71 (s, 3H); 3.46 (s, 2H); 3.40–3.19 (m, 2H); 3.02–2.78 (m, 3H).

EXAMPLE 12

Methyl (3R*,5S*)-(E)-8-(10H,11H-Dibenzo[a,c]-cyclohepten-5-ylidene) -3,5-dihydroxy-6-octenoate By the method of Example 2, the product of the preceding Example (0.44 g, 1.2 mmol) was reduced to present title product. Chromatography on silica gel (2:3 ethyl acetate:hexane as eluant) provided purified product (0.25 g, 56%, mp: 120°–122° C.).

Mass spectra: m/e=378. $^1$H-NMR (CDCl$_3$) delta 7.28–7.0 (m, 8H); 6.50–6.31 (m, 2H); 5.82 (dd, 15, 8Hz, 1H); 4.42–4.20 (m, 2H); 3.72 (s, 3H); 3.4–2.42 (m, 8H). IR (CHCl$_3$) 3472, 2964, 1726 cm$^{-1}$.

EXAMPLE 13

Sodium (3R* 5S*)-(E)-8-(10H,11H-Dibenzo[a,c]-cyclohepten-5-ylidene) -3,5-dihydroxy-6-octenoate By the method of Example 10, the product of the preceding Example (7.8 mg, 0.02 mmol) was converted to present title product, 8 mg tlc (1:1 ethyl acetate:hexane) Rf 0.0 with absence of higher Rf starting material.

EXAMPLE 14

Methyl (E,E)-8,9-Diphenyl-5-hydroxy-3-oxo-6,8-nonadienoate (E,E)-4,5-Diphenyl-2,4-pentadienal (0.5 g) was reacted according to the method of Example 1 to produce present title product, 0.11 g.

Mass spectrum: m/e=350. $^1$H-NMR (CDCl$_3$) delta: 7.28–7.49 (m, 10H); 7.02 (d, 8Hz, 1H); 6.63 (s, 1H); 5.71 (dd, 8, 4Hz, 1H); 4.77 (m, 1H); 3.68 (s, 3H); 3.52 (s, 2H); 2.78–2.83 (m, 2H). IR (CHCl$_3$) 3683, 1744, 1713 cm$^{-1}$.

EXAMPLE 15 612

Methyl (3R*,5S*)-(E,E)-8 9-Diphenyl-3,5-dihydroxy-6,8-nonadienoate

The product of the preceding Example (103 mg) was reacted according to Example 2 to produce present title product, 74 mg.

Mass spectrum: m/e =352. $^1$H-NMR (CDCl$_3$) delta: 7.4–7.2 (m, 10H); 6.92 (d, 8Hz, 1H); 6.55 (s, 1H); 5.66 (dd, 8, 4Hz, 1H); 4.51 (m, 1H); 4.28 (m, 1H); 3.70 (s, 3H); 3.3 (bs, 2H); 2.48–2.4 (m, 2H); 1.77–1.58 (m, 2H). IR (CHCl$_3$) 3478, 1728 cm$^{-1}$.

EXAMPLE 16

Methyl (6E, 8Z) -8,9-Diphenyl-5-hydroxy-3-oxo-6,8-nonadienoate (E,Z)-4,5-Diphenyl-2,4-pentadienal (1.96 g) was reacted according to the method of Example 1 to produce title product, 2.09 g.

Mass spectrum: m/e=350. $^1$H-NMR (CDCl$_3$) delta 7.45–6.88 (m, 10H); 6.72 (d, 8Hz, 1H); 6.65 (s, 1H); 5.32 (dd, 3, 8Hz, 1H); 3.78 (s, 3H); 3.51 (s, 2H); 2.77 (d, 2Hz, 2H). IR (CHCl$_3$) 3656, 1746, 1713 cm$^{-1}$.

EXAMPLE 17

Methyl (3R*,5S*)-(6E,8Z)-8,9-Diphenyl-3,5-dihydroxy-6,8-nonadienoate

The product of the preceding Example (1.10 g) was reacted according to Example 2 to produce present title product, 0.64 g.

Mass spectrum: m/e=352. $^1$H-NMK (CDCl$_3$) delta 6.82–7.43 (m, 10H); 6.68 (d, 8Hz, 1H); 6.02 (s, 1H); 5.32 (dd, 8, 3Hz, 1H); 4.52 (m, 1H); 4.30 (m, 1H); 3.62 (s, 3H); 2.45–2.58 (m, 2H); 1.58–1.72 (m, 2H). IR (CHCl$_3$) 3500, 1725 cm$^{-1}$.

EXAMPLE 18

Methyl (6E,8Z)-8-(8,9-Dihydro-6H, 7H-benzocyclo-hepten-5-ylidene)-5-hydroxy-3-oxo-6-octenoate By the method of Example 1, (2E,4Z)-4-(8,9-dihydro-6H, 7H-benzocyclohepten-5-ylidene)-2-butenal (2.6 g, 12 mmol) was reacted with methyl acetoacetate to form title product, 3.2 g.

Mass spectrum: m/e=328. $^1$H-NMR (CDCl$_3$) delta 7.08–6.98 (m, 4H); 6.22–6.08 (m, 2H), 5.64 (dd, 6, 3Hz, 1H, 1H); 4.50 (m, 1H); 3.72 (s, 3H); 3.47 (s, 2H); 2.78–2.64 (m, 4H); 2.21–2.04 (m, 4H); 1.91–1.60 (m, 4H). IR (CHCl$_3$) 3470, 1750, 1715 cm$^{-1}$. Anal. calcd. for $C_{20}H_{24}O_4$: C, 73.15; H, 7.37. Found: C, 72.72; H, 7.38.

EXAMPLE 19

Methyl (3R*,5S*)-(6E,8Z)-8-(8,9-Dihydro-6H,7H-benzocyclohepten-5-ylidene)-3,5-dihydroxy-6-octenoate By the method of Example 2, the product of the preceding Example (1.0 g, 3.0 mmol) was converted to present title product, 0.9 g.

Mass spectrum: m/e=330. $^1$H-NMR (CDCl$_3$) 7.10–6.99 (m, 4H); 6.19–6.04 (m, 2H); 5.69–5.55 (m, 1H); 4.38–4.15 (m, 2H); 3.66 (s, 3H); 2.72–2.19 (m, 6H); 1.95–1.51 (m, 6H). IR (CHCl$_3$) 3470, 1730 cm$^{-1}$.

EXAMPLE 20

Sodium (3R*,5S*)-(6E,8Z)-8-(8,9-Dihydro-6H 7H-benzocyclohepten-5-ylidene)-3,5-dihydroxy-6-octenoate By the method of Example 10, the product of the preceding Example (0.79 g, 2.4 mmol) was converted to present title product, 0.75 g.

$^1$H-NMR (DMOS-d$_6$) delta: 7.11 (bs, 3H); 6.95–6.99 (m, 1H); 6.14 (d, 6Hz, 1H); 5.96 (dd, 7, 6Hz, 1H); 5.64 (dd, 7, 3Hz, 1H); 4.05–3.98 (m, 1H); 3.71–3.60 (m, 1H); 2.70–2.58 (m, 2H); 2.30–1.21 (m, 12H). IR (KBr) 3894, 1638, 1565 cm$^{-1}$. Anal. calcd. for $C_{19}H_{23}O_4Na \cdot H_2O$: C, 64.04; H, 7.07. Found: C, 63.67; H, 7.52.

EXAMPLE 21

Methyl (E)-8-(Thioxanthen-9-ylidene) -5-hydroxy-3-oxo-6-octenoate

By the method of Example 1, (E)-4-(thioxanthen-9-ylidene)-2-butenal (1.94 g, 7.34 mmol) was reacted with methyl acetoacetate to form present title product, 1.43 g.

Mass spectrum: m/e=380. $^1$H-NMR (CDCl$_3$) delta: 7.20–7.60 (m, 8H); 6.88 (dd, 8, 5Hz, 1H); 6.51 (d, 5Hz, 1H); 6.00 (dd, 8, 3Hz, 1H); 4.72–4.81 (m, 1H); 3.80 (s, 3H); 3.66 (s, 2H); 2.80–2.88 (m, 2H); 2.64 (bs, 1H). IR (CDCl$_3$) 3568, 1743, 1714.

EXAMPLE 22

Methyl (3R*,5S*)-(E)-8-(Thioxanthen-9-ylidene)-3,5-dihydroxy-6-octenoate

By the method of Example 2, the product of the preceding Example (1.40 g, 3.68 mmol) was converted to present title product, 0.35 g.

Mass spectrum: m/e=382. $^1$H-NMR (CDCl$_3$) delta 7.10–7.52 (m, 8H); 6.88 (dd, 8, 6Hz, 1H); 6.44 (d, 6Hz, 1H); 5.92 (dd, 8, 7Hz, 1H); 4.40–4.52 (m, 1H); 4.18–4.31 (m, 1H); 3.70 (s, 1H); 3.11 (bs, 2H); 2.40–2.5 9 (m, 2H); 1.56–1.81 (m, 2H). IR (CHCl$_3$) 3485, 1726 cm$^{-1}$.

EXAMPLE 23

Sodium (3R*,5S*)-(E)-8-(Xanthen-9-ylidene)-3,5-dihydroxy-6-octenoate

By the sequential procedures of Example 1, 2 and 3, (E)-4-(xanthen-9-ylidene)-2-butenal (1 g, 4 mmol) was concentrated to present title product, 0.39 g (26% overall).

$^1$H-NMR (CDCl$_3$) delta: 7.73–6.81 (m, 10H); 6.15 (dd, 14, 5Hz, 1H); 5.06 (bs, 1H); 4.36–4.27 (m, 1H); 3.91–3.78 (m, 1H); 2.25–1.48 (m, 4H). IR (KBr) 3440, 1571 cm$^{-1}$. Anal. calcd. for C$_{22}$H$_{19}$O$_5$Na: C, 67.38; H, 5.12. Found: C, 67.27; H, 5.20.

EXAMPLE 24

Methyl (E)-5-Hydroxy-9,9-di(4-methylphenyl)-3-oxo-6,8-nonadienoate

Using the procedure of Example 1, (E)-5,5-di(4-methylphenyl) 2,4-pentanal (5.03 g, 19.2 mmol) was converted to present title product, 2.31 g.

High resolution mass spectra: m/e found 378.1853, calcd. for C$_{24}$H$_{26}$O$_4$ 278.1831. $^1$H-NMR (CDCl$_3$), delta: 7.22–6.91 (d, 11Hz, 1H); 6.32 (dd, 11, 15Hz, 1H); 5.78 (dd, 6, 15Hz, 1H); 4.55 (dt, 6 & 7Hz, 1H); 3.70 (s, 3H); 3.46 (s, 2H); 2.74 (d, 7Hz, 2H); 2.38 (s, 3H); 2.31 (s, 3H); 2.21 (s, 1H). 13NMR (CDCl$_3$), delta: 202.5, 167.3, 143.8, 139.4, 137.5, 137.2, 136.6, 134.1, 130.2, 129.4, 128.9, 127.5, 125.8, 58.5, 52.4, 51.1, 49.7, 49.6, 21.3, 21.1, 19.3. IR (CHCl$_3$) cm$^{-1}$: 3440, 3360, 3060, 3000, 2980, 2930, 2900, 2850, 1895, 1730, 1695, 1680, 1635, 1600, 1550, 1495, 1470, 1420.

EXAMPLE 25

Methyl (3R*5S*)-(E)-3,5-Dihydroxy-9,9-di(4-methylphenyl)-6,8-nonadienoate

Using the procedure of Example 2, the product of the preceding Example (2.15 g, 5.7 mmol) was converted to present title product, 0.96 g.

High resolution mass sepctra: m/e found 380.1970, calcd. for C$_{24}$H$_{28}$O$_4$ 280.1988. $^1$H-NMR (CDCl$_3$), delta: 7.23–6.91 (m, 8H); 6.56 (d, 12Hz, 1H); 6.30 (dd, 12, 15Hz, 1H); 5.78 (dd, 7, 15Hz, 1H); 4.4–4.29 (m, 1H); 4.27–4.15 (m, 1H); 3.67 (s, 3H);3.03 (br s, 1H); 2.48–2.41 (m, 2H); 2.37 (s, 3H); 2.31 (s, 3H); 1.76–1.51 (m, 3H). $^{13}$C-NMR (CDCl$_3$) delta: 172.8, 143.4, 139.5, 137.3, 137.1, 136.7, 135.9, 130.3, 128.9, 127.5, 126.0, 72.8, 68.3, 51.8, 42.6, 41.5, 21.3, 21.1. IR (CHCl$_3$) cm$^{-1}$: 3410, 3030, 2960, 2930, 2880, 1730, 1515, 1435.

EXAMPLE 26

Methyl (6E,8E)- and (6E,8Z)-8-(Dibenzo[b,e]thiepin 11(6H)-ylidene)-5-hydroxy-3-oxo-6-octenoate By the method of Example 1, a mixture of (2E,4E)- and (2E,4Z-4-(dibenzo[b,e]thiepin-11(6H)-ylidene)-2-butenal (1.58 g, 5.68 mmol) and methyl acetoacetate were converted to a present title product mixture, 0.99 g.

MS (m/e) 394. $^1$H-NMR (CDCl$_3$) delta (ppm) 7.3–7.0 (m, 8H), 6.55–6.43 (m, 1H), 6.2–6.0 (m, 1H), 5.82–4.98 (m, 1H), 4.82–4.55 (m, 2H), 3.7 (s, 3H), 3.54–3.31 (m, 2H), 2.82–2.67 (m, 2H). IR(CHCl$_3$) 3583, 1746, 1713 cm$^{-1}$.

EXAMPLE 27

Methyl (3R*,5S*)-(6E,8E and 6E,8Z)-8-(Dibenzo-[b,e]thiepin-11(6H)-ylidene-3,5-dihydroxy-6-octenoate By the method of Example 2, the title product of the preceding Example (0.99 g, 2.52 mmol) was converted to present title product, 0.71 g.

MS (m/e) 394. $^1$H-NMR (CDCl$_3$) delta (ppm) 7.26–6.95 (m, 8H), 6.51–6.40 (m, 1H), 6.24–6.01 (m, 1H), 5.83–5.74 (m, 1H), 4.86–4.70 (m, 1H), 4.43–4.12 (m, 2H), 3.67 (s, 3H), 3.50–3.30 (m, 2H), 2.58–2.40 (m, 2H), 1.88–1.49 (m, 2H). IR (CHCl$_3$) 3492, 2989, 1726 cm$^{-1}$.

PREPARATION 1

Ethyl (E)-5,5-Diphenyl-2,4-pentadienoate

A 60% dispersion of sodium hydride (3.0 g of dispersion, 1.8 g of NaH, 75 mmol) was washed with anhydrous THF (3×60 ml) and suspended in anhydrous THF (200 ml). The mixture was cooled to 0° C. and triethylphosphonoacetate (15.99 g, 71.3 mmol) was added dropwise via syringe. While stirring at 0° C. for 1 hour, the suspension changed to a clear solution. 3-Phenylcinnamaldehyde (9.9 g, 47.5 mmol) was added dropwise and the resulting mixture was stirred for 1 hour at 0° C. The reaction was quenched by pouring it into water (150 ml). The phases were separated and the aqueous phase was extracted with ether (3×50 ml). The combined organic phases were washed with water (2×50 ml), dried with anhydrous magnesium sulfate, filtered and concentrated in vacuo to give 13.12 g (99% yield) of title product. A sample from this lot (0.350 g) was purified by PTLC (2:3 ether:hexane) to give 0.290 g (83% recovery) of pure product.

High resolution mass spectra: m/e found 278.1276, calcd. for $C_{19}H_{18}O_2$ 278.1307. $^1$H-NMR (CDCl$_3$) delta: 7.44–7.20 (m, 11H); 6.78 (d, 12Hz, 1H); 6.04 (d, 15Hz, 1H); 4.08 (q, 7Hz, 2H); 1.14 (t, 7Hz, 3H). 13C NMR (CDCl$_3$), delta: 167.1, 150.8, 142.2, 141.4, 138.6, 130.4, 128.7, 128.1, 125.4, 122.4, 60.2, 14.3. IR (CHCl$_3$) cm$^{-1}$: 3046, 2976, 1697, 1616, 1270.

PREPARATION 2

(E)-5,5-Diphenyl-2,4-pentadien-1-ol

To a −40° C. solution of the product of the preceding Preparation (12.8 g, 46 mmol) in anhydrous THF (250 ml) was added 1M diisobutylaluminum hydride in hexanes (122.3 ml, 122.3 mmol) dropwise via syringe. The reaction mixture was stirred at −40° C. for 2 hours, then cautiously quenched by dropwise addition of ethanol (22 ml). The cooling bath was removed and saturated aqueous sodium chloride (45 ml) was added. The resulting mixture was diluted with ether (450 ml) and stirred at room temperature for 1 hour. A gelatinous solid formed during this period. The mixture was dried with anhydrous magnesium sulfate, filtered through diatomaceous earth and concentrated in vacuo to give 13.1 g of crude product. Purification by flash chromatography (1: 4 ethyl acetate:hexane) gave 9.2 g (85% yield) of title product, which was sufficiently pure to be used in the next step.

A sample of this lot (0.300 g) was further purified by PTLC (1:2 ether:hexane) to give 0.276 g (82% recovery) of material which gave the following spectral data. High resolution was mass spectra: m/e found 236.1216, calcd. for $C_{17}H_{16}O$ 236.1201. $^1$H-NMR (CDCl$_3$), delta: 7.40–7.20 (m, 10H); 6.85 (d, 12Hz, 1H); 6.35 (ddt, 15, 12, 1Hz, 1H); 6.00 (dt, 15, 7Hz, 1H); 4.17 (ddd, 7, 7 & 1Hz, 2H); 1.68 (t, 7Hz, 1H). $^{13}$C-NMR (CDCl$_3$) delta: 143.2, 139.5, 133.7, 130.4, 129.6, 128.2, 128.2, 127.5, 127.4, 127.0, 63.6. IR (CHCl$_3$) cm$^{-1}$: 3667, 3592, 3033, 2990, 2920, 1600.

PREPARATION 3

(E)-5,5-Diphenyl-2,4-pentadien-1-ol

To a −78° C. solution of oxalyl chloride (5.94 g, 46.8 mmol) in anhydrous methylene chloride (100 ml) was added dimethyl sulfoxide (7.03 g, 90 mmol)dropwise. After stirring at −78° C. for 30 minutes, this mixture was added via cannula to a −78° C. solution of the product of the preceding Preparation (8.70 g, 36.8 mmol) in anhydrous methylene chloride (100 ml). After stirring at −78° C. for 3 hours, triethylamine (29 ml, 205 mmol) was added and the resulting mixture was stirred for an additional 30 minutes. The mixture was allowed to warm to room temperature and diluted with 1:4 methylene chloride:hexane (600 ml). The resulting mixture was washed with 10% aqueous sodium bisulfate (4×200 ml) and water (2×100 ml), dried with sodium sulfate, filtered and concentrated in vacuo to give 8.85 g of crude product. Purification by flash chromatography (1:4 ethyl acetate:hexane) gave 3.98 g (46% yield) of title product as a yellow solid, mp 71°–72° C.

High resolution mass spectra: m/e found 234.1041, calcd. for $C_{17}H_{14}O$ 234.1045. $^1$H-NMR (CDCl$_3$), delta: 9.46 (d, 9Hz, 1H); 7.42–7.20 (m, 10H); 7.20–7.17 (dd, 15, 12Hz, 1h); 6.94 (d, 12Hz, 1H), 6.30 (dd, 15 & 9Hz, 1H). $^{13}$C-NMR (CDCl$_3$) delta: 193.9, 153.2, 149.8, 140.9, 138.4, 132.5, 130.5, 129.8, 129.3, 128.8, 128.7, 128.4, 128.2, 127.6, 127.5, 127.4, 127.3. IR (CHCl$_3$) cm$^{-1}$: 3000, 1720, 1598, 1205.

PREPARATION 4

(E)-5,5-Diphenyl-2,4-pentadienal

To a −78° C. solution of (Z)-1-ethoxy-2-tri-n-butyl-stannylethylene (17.85 g, 49.3 mmol) in anhydrous THF (250 ml) was added a solution of n-butyllithium in hexane (23.8 ml, 2.5M, 59.5 mmol) dropwise via syringe. The resulting solution was stirred at −78° C. for 1 hour, then a solution of 3-phenylcinnamaldehyde (7.0 g, 33.6 mmol) in anhydrous THF (100 ml) was added via syringe. The resulting bright purple solution was stirred at −78° C. for 4 hours, then allowed to warm to room temperature. The mixture was quenched with saturated aqueous sodium bicarbonate (200 ml), allowed to stir 10 minutes and diluted with water (300 ml). The phases were separated and the aqueous phase was extracted with ether. The combined organic phases were dried with anhydrous magnesium sulfate, filtered and concentrated in vacuo to give 7.75 g of crude product. Purification by flash chromatography (1:3 ethyl acetate:hexane) gave 4.46 g (56.7% yield) of title product having properties identical to those of the preceding Preparation.

PREPARATION 5

Ethyl (E)-5,5-Di(4-chlorophenyl)-2,4-pentadienoate

By the method of Preparation 1,4,4'-dichlorobenzophenone (5.00 g, 19.9 mmol) was hologated using triethyl 4-phosphonocrotonate (5.23 g, 20.9 mmol) and sodium hydride (0.528 g, 22 mmol) to give, after purification, 1.94 g (28% yield) of title product, mp 99°–100° C.

High resolution mass spectra: m/e found 346.0535, calcd. for $C_{19}H_{16}C_{12}O_2$ 346.0527. 1H-NMR (CDCl$_3$) delta: 7.40–7.04 (m, 9H); 6.72 (d, 12Hz, 1H); 6.04 (d, 14Hz, 1H); 4.16 (q, 7Hz, 2H); 1.25 (t, 7Hz, 3H). $^{13}$C-NMR (CDCl$_3$) delta: 166.9, 148.1, 141.2, 139.4, 136.6, 134.8, 134.6, 131.7, 129.3, 128.8, 128.7, 26.0, 123.4, 60.4, 14.3. IR(CHCl$_3$) cm$^{-1}$: 3050, 2980, 2900, 1710, 1620, 1495.

PREPARATION 6

(E)-5,5-Di(4-chlorophenyl)-2,4-pentadien-1-ol

By the procedure of Preparation 2, the product of the preceding Preparation (1.84 g, 5.3 mmol)was reduced to give 1.42 g (88% yield) of present title product, mp 119°–120° C.

High resolution mass spectra: m/e found 304.0200, calcd. for $C_{17}H_{14}Cl_2O$. $^1$H-NMR (CDCl$_3$) delta: 7.48–7.05 (m, 8H); 6.66 (d, 11Hz, 1H); 6.30 (dd, 15, 11Hz, 1H); 6.06 (dt, 6, 15Hz, 1H); 4.17 (d, 6Hz, 2H); 1.45 (s, 1H). $^{13}$C-NMR (CDCl$_{13}$) delta: 140.6, 140.1, 137.5, 134.9, 133.6, 133.5, 131.6, 128.7, 128.6, 128.5, 127.9, 63.4. IR (CHCl$_3$) cm$^{-1}$: 3240, 2880, 2830, 1595, 1495.

PREPARATION 7

(E)-5,5-Di(4-chlorophenyl)-2,4-pentadienal

By the procedure of Preparation 3, the product of the preceding Preparation (1.34 g, 4.4 mmol) was oxidized to give 1.34 g (100% yield) of present title product.

High resolution mass spectra: m/e found 302.0208, calcd. for $C_{17}H_{12}Cl_2O$ 302.0265. $^1$H-NMR (CDCl$_3$) delta: 9.45 (d, 8Hz, 1H); 7.46–7.05 (m, 9H); 6.89 (d, 12Hz, 1H); 6.30 (dd, 8, 15Hz, 1H). $^{13}$C-NMR (CDCl$_3$) delta: 193.5, 150.2, 148.5, 138.8, 136.2, 135.5, 135.1, 133.2, 131.6, 129.4, 129.3, 129.0, 128.8, 125.9. IR (CHCl$_3$) cm$^{-1}$: 3020, 2940, 2800, 2710, 1660, 1590, 1570, 1475.

PREPARATION 8

Ethyl (E)-5,5-Di(4-fluorophenyl)-2,4-Pentadienoate

By the procedure of Preparation 5, 4,4'-difluorobenzophenone (12.00 g, 55.0 mmol) was homologated to give 3.26 g (19% yield) of present title product.

High resolution mass spectra: m/e found 314.1116, calcd. for C$_{19}$H$_{16}$F$_2$O$_2$ 314.1119. $^1$H-NMR (CDCl$_3$) delta: 7.38–6.94 (m, 9H); 6.71 (d, 12Hz, 1H); 6.04 (d, 15Hz, 1H); 4.16 (q, 7Hz, 2H); 1.25 (t, 7Hz, 3H). $^{13}$C-NMR (CDCl$_3$) delta: 167.0, 166.9, 164.7, 164.4, 161.1, 148.5, 141.6, 137.4, 137.3, 134.4, 134.3, 132.1, 132.0, 129.9, 129.7, 125.4, 122.7, 115.7, 115.5, 115.3, 60.3, 14.2 (fluorine not decoupled). IR (CHCl$_3$) cm$^{-1}$ 3330, 3070, 3050, 2990, 2900, 1705, 1625, 1605, 1515.

PREPARATION 9

(E)-5,5-Di-(4-fluorophenyl)-2,4-pentadien-1-ol

By the procedure of Preparation 2, the product of the preceding Preparation (4.97 g, 15.8 mmol) was reduced to give 4.02 g (93% yield) of present title product, mp 109°–110° C.

High resolution mass spectra: m/e found 272.1001, calcd. for C$_{17}$H$_{14}$F$_2$O 272.1012. $^1$H-NMR (CDCl$_3$) delta: 7.26–6.91 (m, 8H); 6.63 (d, 12Hz, 1H); 6.28 (dd, 15 and 12Hz, 1H), 6.01 (dt, 15 and 6Hz, 1H); 4.16 (d, 6Hz, 2H); 1.46 (s, 1H). $^{13}$C-NMR (CDCl$_3$) delta: 163.9, 160.8, 160.6, 140.9, 138.1, 138.0, 135.3, 135.2, 134.1, 132.0, 129.1, 129.0, 128.9, 127.2, 115.5, 115.3, 115.2, 115.0, 63.4 (fluorine not decoupled). IR (CHCl$_3$) cm$^{-1}$: 3240, 3050, 3012, 2890, 2840, 1645 1605, 1510, 1450.

PREPARATION 10

(E)-5,5-Di(4-fluorophenyl)-2,4-pentadienal

By the procedure of Preparation 3, the product of the preceding Preparation (2.81 g, 10.3 mmol) was oxidized to give 1.09 g (39% yield) of present title product, mp 121°–122° C.

High resolution mass spectra: m/e 270.0868, calcd. for C$_{17}$H$_{12}$F$_2$O 270.0856. $^1$H-NMR (CDCl$_3$) 9.44 (d, 7Hz, 1H); 7.31–6.95 (m, 9H); 6.84 (d, 12Hz, 1H); 6.28 (dd, 15 and 7Hz, 1H). $^{13}$C-NMR (CDCl$_3$) delta: 193.6, 165.0, 164.6, 161.7, 161.3, 150.6, 148.9, 136.9, 134.1, 132.8, 132.1, 130.1, 130.0, 125.3, 115.9, 115.7, 115.6, 115.5 (fluorine not decoupled). IR (CHCl$_3$) cm$^{-1}$: 3070, 2810, 2730, 1670, 1595, 1505, 1415.

PREPARATION 11

4-(8,9-Dihydro-6H,7H-benzocyclohepten-5-ylidene)-2-buten-1-ol

By the method of Preparation 2, except to quench into saturated NH$_4$Cl and extract into ethyl acetate, methyl 4-(8,9-dihydrobenzocyclohepten-5-ylidene)-2-butenoate (7.7 g., 0.032 mol) was reduced to yield present title product which was recrystallized from isopropyl ether (3.8 g, 56%, mp: 108°–109° C.). $^1$H-NMR (CDCl$_3$) delta: 7.61 (d, 7Hz, 1H); 7.25–7.02 (m, 3H); 5.51–5.79 (m, 2H); 4.02 d, 4Hz, 2H); 2.39–3.01 (m, 6H); 1.80–2.01 (m, 4H). Anal Calcd. for C$_{15}$H$_{20}$O$_2$: C, 7.55; H, 8.68. Found: C, 77.72; H, 8.69.

PREPARATION 12

(E,E)-4-(8,9-Dihydro-6H,7H-benzocyclohepten-5-ylidene)-2-butenal and
(E,Z)-4-(8,9-Dihydro-6H,7H-benzocyclohepten-5-ylidene)-2-butenal Oxalyl chloride (3.8 ml, 0.043 mol) was placed in a dry flask under nitrogen, dissolved in dry tetrahydrofuran and cooled to −78° C. Dry dimethyl sulfoxide (5.5 ml, 0.078 mol) was added slowly dropwise by a syringe. After stirring for 5 minutes at −78° C., this solution was cannulated into a solution of the product of the preceding Preparation (8.5 g, 0.037 mol) in dry tetrahydrofuran (20 ml) at −78° C. and stirred for 1 hour. Triethyl amine (25 ml) was added and the mixture was stirred for an additional hour, warmed to 25° C., poured into methylene chloride (160 ml), washed with 10% sodium bicarbonate, water and brine and dried over magnesium sulfate. After filtering and concentrating, the residue was dissolved in tetrahydrofuran (50 ml) and treated with concentrated HCl (2 ml). After heating on a steam bath for 0.75 hour, the reaction was diluted with ether (200 ml), washed with water, NaHCO$_3$ and brine, dried over magnesium sulfate and concentrated in vacuo to a brown oil. Chromatography on silica gel (1:1, ethyl acetate:hexane as eluant) provided (E,E) title product (2.6 g) and (E,Z) title product (2.4 g).

(E,E)-Product: Mass spectrum: m/e=212. $^1$H-NMR (CDCl$_3$) 9.61 (d, 4Hz, 1H); 7.54 (dd, 7, 6Hz, 1H); 7.26–7.04 (m, 4H); 6.36 (d, 6Hz, 1H); 6.21 (dd, 7, 4Hz, 1H); 2.66–2.81 (m, 4H); 1.91–1.79 (m, 4H).

(E,Z)-Product: Mass spectrum: m/e=212. $^1$H-NMR (CDCl$_3$) 9.34 (d, 4Hz, 1H); 6.98–7.24 (m, 5H); 6.44 (d, 6Hz, 1H); 6.11 (dd, 8, 4Hz, 1H); 2.72 (m, 2H); 2.46 (m, 2H); 1.62–1.98 (m, 4H).

PREPARATION 13

(10H,11H-Dibenzo[a,c]cyclohepten-5-ylidene)acetaldehyde

Dibenzosuberone (5.3 g, 0.026 mol) was reacted with 1-ethoxy-2-lithio ethylene in anhydrous THF in the manner of Preparation 1 to yield present title product as a yellow oily solid, 2.86 g ( 48% ).

$^1$H-NMR (CDCl$_3$) 9.59 (d, 7Hz, 1H); 7.2–7.0 (m, 8H); 6.45 (d, 7Hz, 1H); 3.42–2.79 (m, 4H).

PREPARATION 14

(E)-4-(10H,11H-Dibenzo[a,c]cyclohepten-5-ylidene)-2-butenal

The product of the preceding Preparation was reacted with 1-ethoxy-2-lithio ethylene in like manner to yield present title product, 2.26 g (71%) as a foam.

$^1$H-NMR (CDCl$_3$) delta 9.48 (d, 8Hz, 1H); 7.22–7.01 (m, 8H); 6.95 (d, 10Hz, 1H); 6.30 (dd, 10, 8Hz, 1H); 3.44–2.80 (m, 4H). IR (CHCl$_3$) 2916, 2816, 1673, 1611 cm$^{-1}$. MS (m/e) 212.

PREPARATION 15

(E)-4-(Xanthen-9-ylidene)-2-butenal

By the procedure of Preparation 4, (9-xanthenylidene)acetaldehyde (Wizinger et al., Chem. Bet. 92, pp. 2309–2320 (1959); 4.5 g, 0.20 mmol) was converted to present title product, 2.19 g (44%).

$^1$H-NMR (CDCl$_3$) delta 9.62 (d, 4Hz, 1H); 7.93–6.88 (m, 9H); 6.73 (d, 6Hz); 6.38 (dd, 7, 3, 1H).

PREPARATION 16

3,3-Di(4-methylphenyl)acrolein

By the procedure of Preparation 4, 4,4'-dimethylbenzophenone (15.0 g, 71.3 mmole) was converted to 3,3-di(4-methylphenyl)acrolein 8.06 g, mp 82°–83° C.

High resolution mass spectra: m/e found 236.1207, calc. for $C_{17}H_{16}O$ 236.1201. $^1$H-NMR (CDCl$_3$) delta: 9.48 (d, 8Hz, 1H); 7.32–7.11 (m, 8H); 6.53 (d, 8Hz, 1H); 2.42 (s, 3H); 2.38 (s, 3H). $^{13}$C-NMR (CDCl$_3$) delta: 193.7, 162.5, 140.9, 139.6, 137.1, 133.9, 130.7, 129.3, 128.9, 128.7, 126.4, 21.3. IR (CHCl$_3$) cm$^{-1}$; 3030, 2920, 2830, 1660, 1615, 1595, 1510.

PREPARATION 17

Ethyl (E)-5,-Di(4-methylphenyl)-2,4-pentadienoate

By the procedure of Preparation 1, the product of the preceding Example (7.55 g, 32.0 mmol) was converted to present title product, 8.34 g.

High resolution mass spectra: m/e found 306.1607, calcd. for $C_{21}H_{22}O_2$ 306.1620. $^1$H-NMR (CDCl$_3$) delta: 7.37 (dd, 11, 16Hz, 1H); 7.24–7.02 (m, 8H); 6.71 (d, 11Hz, 1H); 5.99 (d, 16Hz, 1H); 4.15 (q, 6Hz, 1H); 2.40 (s, 3H); 2.34 (s, 3H); 1.25 (t, 6H). $^{13}$C-NMR (CDCl$_3$) delta: 167.2, 150.9, 142.6, 138.8, 138.6, 138.0, 135.6, 130.3, 129.0, 128.9, 128.1, 124.4, 121.5, 60.1, 21.6, 21.2, 14.6. IR (CHCl$_3$) cm$^{-1}$: 3030, 300, 2960, 2900, 2850, 1695, 1685, 1600, 1590, 1500, 1450, 1440, 1435.

PREPARATION 18

(E)-5,5-Di(4-methylphenyl)-2,4-pentadien-1-ol

By the method of Preparation 2, the product of the preceding Preparation (8.25 g, 26.9 mmol) was converted to present title product , 7.11 g; mp 82°–83° C.

High resolution mass spectra: m/e found 263.1501, calcd. for $C_{19}H_{20}O$ 264.1514. $^1$-NMR (CDCl$_3$) delta: 7.22–7.01 (m, 8H); 6.63 (d, 11Hz, 1H); 6.32 (dd, 11, 14Hz, 1H); 5.96 (dt, 6, 14Hz, 1H); 4.12 (d, 6Hz, 2H); 2.38 (s, 3H); 2.32 (s, 3H); 1.56 (s, 1H). $^{13}$C-NMR (CDCl$_3$) delta: 143.2, 139.5, 137.3, 136.7, 136.4, 132.9, 130.3, 129.9, 128.9, 127.5, 126.1, 63.6, 21.3, 21.1. IR (CHCl$_3$) cm$^{-1}$: 3330, 3070, 3010, 2900, 2850, 1900, 1780, 1655, 1635, 1600, 1500, 1440, 1400.

PREPARATION 19

(E)-5,5-Di(4-methylphenyl)-2,4-pentadienal

By the method of Preparation 3, the product of the preceding Preparation (5.85 g, 22.1 mmol) was converted to present title product, 5.5 g, mp 92°–93° C.

High resolution mass spectra: m/e found 262.1336, calcd. for $C_{19}H_{18}O$ 262. 1358. $^1$H-NMR (CDCl$_3$) delta: 9.40 (d, 8Hz, 1H); 7.26–7.04 (m, 9H); 6.84 (d, 12Hz, 1H); 6.24 (dd, 8, 16Hz, 1H); 4.42 (s, 3H); 4.35 (s, 3H). $^{13}$C-NMR (CDCl$_3$) delta: 193.0, 153.4, 150.4, 139.5, 138.6, 138.2, 135.5, 131.9, 130.4, 129.2, 128.3, 124.3, 21.4, 21.3. IR (CHCl$_3$) cm$^{-1}$: 3310, 3010, 2900, 2850, 2790, 2700, 1900, 1665, 1655, 1595, 1585, 1440, 1400.

PREPARATION 20

(E,E)-4,5-Diphenyl-2,4-pentadienal

By the method of Preparation 4, (E)-2-phenylcinnamaldehyde (3.91 g) was converted to present title product, 0.5 g.

Mass spectrum: m/e=233. $^1$H-NMR (CDCl$_3$) delta: 9.68 (d, 4H, 1H); 7.84 (d, 8Hz, 1H); 7.58–7.32 (m, 10H); 7.50 (s, 1H); 6.22 (dd, 8, 4Hz, 1H). IR (CDCl$_3$) 1676, 1609, 1130 cm$^{-1}$.

PREPARATION 21

(2E, 4Z)-4,5-Diphenyl-2,4-pentadienal

By the method of Preparation 4, (Z)-2-phenylcinnamaldehyde (3.94 g) was converted to present title product, 2.02 g.

Mass spectrum: m/e=233. $^1$H-NMR (CDCl$_3$) delta: 9.67 (d, 4Hz, 1H); 7.50–6.98 (m, 12H); 5.82 (dd, 7, 4Hz, 1H). IR (CHCl$_3$) 1672, 1608, 1572, 1392, 1103, 970 cm$^{-1}$.

PREPARATION 22

(2E,4E)- and (2E,4Z)-4-(Dibenzo[b,e]thiepin-11(6H)-ylidene)-2-butenal

To a solution of 1-tri-n-butylstannyl-4-ethoxybutadiene (5.0 g, 12.9 mmol, Wollenberg, Tetrahedron Lett. p. 717, 1978) in dry THF (40 ml) in a dry flask under nitrogen atmosphere was added n-butyllithium (1.6M in hexanes, 8.4 ml) while cooling at $-78°$ C. After stirring at $-78°$ C. for 5 minutes, 6,11-dihydrobenzo[b,e]thiepin-11(6H)one (2.65 g, 11.7 mmol; Stach et al. Angew. Chem., vol. 74, p. 752, 1962) in THF (8 ml) was added. After stirring for 1 hour, the reaction was quenched with NH$_4$Cl (20 ml) and allowed to come to room temperature over 18 hours. The reaction was partitioned between ethyl acetate and 3N HCl with occasional shaking for 0.5 hours. Chromatography on silica gel (ethyl acetate:hexanes, 1:10) provided 1.2 g of title products as a foam as a mixture of geometric isomers Mass spectrum: m/e=278. IR (CHCl$_3$) 1674, 1612, 1150 cm$^{-1}$.

We claim:

1. A compound having the following stereochemical formula

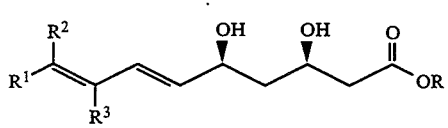

wherein R is hydrogen, (C$_1$–C$_3$)alkyl, phenyl, benzyl or a conventional radical forming an ester group which is hydrolyzable under physiological conditions;

R$^1$ and R$^2$, when taken separately, and R$^3$ are each independently hydrogen, (C$_1$–C$_3$)alkyl, benzyl, naphthyl, phenyl or phenyl mono or disubstituted with the same or different substituents selected from the group consisting of F, Cl, Br, I, (C$_1$–C$_3$)alkyl, CF$_3$, (C$_1$–C$_3$)alkoxy, benzyl and phenyl; with the proviso that at least one of R$^1$ and R$^2$ is other than hydrogen or (C$_2$–C$_3$)alkyl; and R$^1$ and R$^2$, when taken together, are combined with the double bonded carbon atom to which they are attached to form a diradical ylidene group of the formula

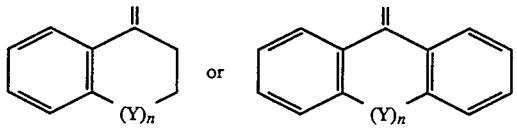

wherein n is 0 or 1 and Y is oxygen, $OCH_2$, sulfur, $SCH_2$, methylene or ethylene; with the proviso that $R^1$ and $R^2$ are taken together when R is hydrogen, $(C_1-C_3)$ alkyl, phenyl or benzyl; or a pharmaceutically acceptable cationic salt thereof when R is hydrogen.

2. A compound of claim 1 wherein R is a conventional radical forming an ester group which is hydrolyzable under physiological conditions selected from the group consisting of:

furan-5(1H)-on-1-yl;
isobenzofuran-3(1H)-on-1-yl;
3,4-dihydrofuran-5(1H)-on-1-yl;
—$CHR^4OCOR^5$; and
—$CHR^4OCOOR^5$;
wherein
$R^4$ is hydrogen or methyl; and
$R^5$ is $(C_1-C_6)$alkyl.

3. A compound of claim 1 wherein R is hydrogen, $(C_1-C_3)$alkyl, phenyl or benzyl.

4. A compound of claim 3 wherein R is hydrogen or methyl and $R^3$ is hydrogen.

5. The compound of claim 4 wherein R is methyl and $R^1$ and $R^2$ are taken together with the double bonded carbon to which they are attached to form a 9-xanthenylidene group.

6. The compound of claim 4 wherein R is hydrogen and $R^1$ and $R^2$ are taken together the double bonded carbon to which they are attached to form a 9-xanthenylidene group.

7. The compound of claim 4 wherein R is hydrogen and $R^1$ and $R^2$ are taken together to form a 8,9-dihydro-6H-benzocyclohepten-5 (7H)ylidene group.

8. A pharmaceutical composition for the treatment or prevention of atherosclerosis in a mammal which comprises a blood cholesterol lowering effective amount of a compound of claim 1.

9. A pharmaceutical composition for the treatment or prevention of atherosclerosis in a mammal which comprises a blood cholesterol lowering effective amount of a compound of claim 4.

10. A method of treating or preventing atherosclerosis in a mammal which comprises administering a blood cholesterol lowering effective amount of a compound of claim 1 to said mammal.

11. A method of treating or preventing atherosclerosis in a mammal which comprises administering a blood cholesterol lowering effective amount of a compound of claim 4 to said mammal.

* * * * *